United States Patent [19]
Chae et al.

[11] Patent Number: 5,472,694
[45] Date of Patent: Dec. 5, 1995

[54] METHOD FOR MANUFACTURING TEA BY TREATING THE LEAVES OF CYCLOBALANOPSIS STENOPHYLLA

[76] Inventors: Han Y. Chae, #106, Dong-A APT, 512-4, Anyang-6 Dong, Anyang City, Kyungki-Do; Baek H. Sik, #1032-4, Doksan-2 Dong, Kuro-ku, Seoul, both of Rep. of Korea

[21] Appl. No.: 139,921

[22] Filed: Oct. 20, 1993

[30] Foreign Application Priority Data

Mar. 24, 1993 [KR] Rep. of Korea .................. 93-4574

[51] Int. Cl.$^6$ .................................................. A61K 75/78
[52] U.S. Cl. ..................... 424/195.1; 424/597; 424/615; 424/648
[58] Field of Search ............ 424/195.1; 426/597, 426/615, 648

[56] References Cited

U.S. PATENT DOCUMENTS 4,912,089  3/1990  Hiji ............................................ 514/25

*Primary Examiner*—John W. Rollins
*Attorney, Agent, or Firm*—Ladas & Parry

[57] ABSTRACT

The present invention relates to a method for manufacturing tea by treating the leaves of cyclobalanopsis stenophylla. The leaves of cyclobalanopsis stenophylla are collected in May or June and, directly thereafter, are treated with steam for 50±10 minutes. When their green color changes into a yellowish brown and a savory smell is given out, they are taken out and desiccated in the shade and, then, based on volume, 5% to 10% of glutinous rice or polished glutinous millet is mixed in 90% to 95% of water and put in the bottom of a steamer. A bored plate is placed on the steamer, and the desiccated leaves are put down on the plate and treated for 20±5 minutes with steam generated by applying heat to the steamer and the leaves treated with steam are desiccated again and made into tea.

2 Claims, No Drawings

METHOD FOR MANUFACTURING TEA BY TREATING THE LEAVES OF CYCLOBALANOPSIS STENOPHYLLA

FIELD AND BACKGROUND OF THE INVENTION

The present invention relates to a method for manufacturing tea by treating the leaves of cyclobalanopsis stenophylla (Fagaceae), also known as Quercus salicina.

The cyclobalanopsis stenophylla is an evergreen tree which belongs to Fagaceae. Its leaves are elliptical, somewhat long and cuspidated. The edge of the leaf is sawtoothed. The veins in the center of the leaf, and the back thereof is white as if there is a layer of powder thereon.

It is known that cyclobalanopsis stenophylla when taken as a folk remedy and after it has been decocted, dissolves a calculus such as a biliary calculus or a renal calculus and discharges it from the body. In 1958, its medical benefits as a litholysis agent were experimentally proved for the first time at a medical school of a Japanese University (Tokushima University). In 1966, its medical benefits were again proved effective as a result of an experiment conducted by the Tokyo University.

It is generally known that flavonoid (quercetin, kaempferol, isoquercitrin), tannin (ellagic acid 3, 3'-di-o-methylellagic acid, β-D-glucongallin, catechol, pyrogallol, gallic acid), fatty acid (succinic acid), threeterpene (fridelin, friedelanol, epifriedelanol) are constituent parts of the cyclobalanopsis stenophylla leaf.

It has been shown that a 10% sinking solution of the cyclobalanopsis stenophylla leaf dissolved 50% to 90% of a calculus comprised of cholesterol and stearic acid. Although it was stated that such dissolution was by catechol tannin, the accurate mechanism of dissolving a calculus is still the object of scientific study which must be revealed because other fatty acids are present in addition to tannin.

It has also been revealed by a clinical demonstration and an animal experiment that the sinking solution of the cyclobalanopsis stenophylla leaf was stable as a folk medicine because it produced no effect on bile secretion, breathing and blood pressure. The essence extracted by boiling the leaves of cyclobalanopsis stenophylla is used as tea. Also, tea made from an extract of its leaf has been placed on the market.

DESCRIPTION OF THE INVENTION

A method for treating the leaves of cyclobalanopsis stenophylla according to the present invention improves its efficiency as a litholysis agent by preventing the constituent parts of the leaf from changing and making it possible to keep it stored for a long period of time as compared with a method for manufacturing tea from an extract of the useful ingredients by conventional sinking. Accordingly, one aspect of the present invention provides a method for manufacturing leaf tea of cyclobalanopsis stenophylla which improves its efficiency as a lytholysis agent.

A method according to the present invention will now be described.

In May and June, the leaves of cyclobalanopsis stenophylla are collected and treated with aqueous vapor for 50±10 minutes before desiccation. As soon as chlorophyll is saccharized or directly after the green color changes into yellowish brown and the smell of fresh young greens is not given out, but a savory smell is emitted, they (the leaves) are taken out and desiccated in ventilated shade. Then, based on volume, 5% to 10% of glutinous rice or polished gluninous millet and 90% to 95% of water are mixed together and put in the bottom of a steamer. Thereafter, a bored plate is placed on the steamer and covered with the desiccated leaves. Those leaves are heated for 20±5 minutes with steam generated by applying heat to the steamer. The steamed leaves are made into tea after desiccation.

The amount of time the leaves are treated with steam directly after collection may vary according to the time of harvest, the amount of rainfall and the duration of sunshine.

The leaves of cyclobalanopsis stenophylla can be desiccated not using air. In this case, however, the leaves must not be carbonized by excessive desiccation. It is proper that the moisture content amounts to 11% or 12% at this time.

When the leaves are desiccated excessively during storage, they are liable to be destroyed by a physical shock. They degenerate and ferment by the activation of a group of enzymes. As they go bad as a result thereof, they must preferably be kept in the ventilated and cool shade.

One must be careful to ensure that water does not touch the leaves of cyclobalanopsis stenophylla for the reason that useful ingredients thereof must be preserved by the dissolution of tannin contained in the fresh leaf due to an excess of steam when the leaves are treated with steam for the second time.

When the leaves of cyclobalanopsis stenophylla are desiccated after treatment with steam, a group of enzymes is inactivated and their self-digestion is kept under control. Accordingly, the leaves are prevented from withering. The composition of a leaf is also prevented from changing even when kept in storage for a long period of time.

When the desiccated leaves are treated with steam, glutinous rice or polished glutinous millet mixed in water is saccharized and the highly concentrated constituent parts thereof are held on to the leaves like gelatin to protect those leaves. When these leaves are decocted and taken as tea, they have a good taste.

It improves the efficiency of tea as a litholysis agent to decoct the leaves at 75° C. to 85° C. so as not to affect their useful ingredients when decocted for drinking as tea.

The present invention also relates to a method for manufacturing the leaf tea of cyclobalanopsis stenophylla, the method comprising collecting the leaves of cyclobalanopsis stenophylla and treating them with steam for between 40 and 60 minutes. The leaves are the desiccated in the shade. Thereafter, 5%–10% glutinous rice or polished glutinous millet, and water amounting to 90%–95% in terms of volume, are mixed and put into a steamer. A board plate is placed on the steamer and the desiccated leaves are put down on the plate and treated for 15–25 minutes with steam generated by applying heat to the steamer. The steam treated leaves are desiccated again and made into tea.

EXAMPLE

The leaves of cyclobalanopsis stenophylla are collected in May and June. Directly after collection, those leaves are treated with steam for 50±10 minutes. When the green color of these leaves changes into yellowish brown and a savoring smell is given out, they are taken out and desiccated in the ventilated shade. Then, based on volume, 5% to 10% of glutinous rice or polished glutinous millet from 90% to 95% of water are mixed and put in the bottom of a steamer and a bored plate is placed on the steamer. It is enough that holes are bored in the plate so as to keep the leaves from falling into the steamer. The desiccated leaves are put down on the plate and steamed for 20±5 minutes with steam generated by applying heat to the steamer. The leaves treated with steam are desiccated again and made into tea.

What is claimed is:

1. A method for manufacturing the leaf tea of cyclobalanopsis stenophylla, comprising:

collecting the leaves of cyclobalanopsis stenophylla in May and/or June;

directly thereafter, steam treating the leaves for approximately 40 to 60 minutes until the leaves change from a green color into a yellowish brown color and a savory smell is emitted;

removing the leaves from the steam treatment and desiccating them in shade;

mixing, by volume, 5% to 10% glutinous rice and/or polished glutinous millet in 90% to 95% water and placing the mixing at the bottom of a steamer;

locating a bored plate on the steamer; and placing the desiccated leaves on the bored plate for approximately 15 to 25 minutes and treating the leaves with steam generated by applying heat to the steamer so that the leaves treated thereby are desiccated once more and made into tea.

2. The method as claimed in claim 1 wherein the mixture comprises about 5% glutinous rice and/or polished glutinous millet and approximately 90% to 95% water, by volume.

* * * * *